United States Patent
Moffitt et al.

(10) Patent No.: US 9,440,079 B2
(45) Date of Patent: Sep. 13, 2016

(54) MANAGEMENT OF STIMULATION SAFETY LIMITS IN A NEUROSTIMULATION SYSTEM

(75) Inventors: Michael A. Moffitt, Valencia, CA (US); Sridhar Kothandaraman, Valencia, CA (US); David K. L. Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 777 days.

(21) Appl. No.: 13/470,328

(22) Filed: May 13, 2012

(65) Prior Publication Data

US 2012/0290040 A1 Nov. 15, 2012

Related U.S. Application Data

(60) Provisional application No. 61/486,120, filed on May 13, 2011.

(51) Int. Cl.
| | |
|---|---|
| *A61N 1/37* | (2006.01) |
| *A61N 1/36* | (2006.01) |
| *A61N 1/372* | (2006.01) |

(52) U.S. Cl.
CPC ....... *A61N 1/36142* (2013.01); *A61N 1/37241* (2013.01); *A61N 1/36185* (2013.01)

(58) Field of Classification Search
CPC ..................... A61N 1/36142; A61N 1/37241; A61N 1/36185
USPC .............................................. 607/45, 59, 63
See application file for complete search history.

(56) References Cited

U.S. PATENT DOCUMENTS

| | | | |
|---|---|---|---|
| 4,392,496 A | 7/1983 | Stanton | |
| 5,470,347 A * | 11/1995 | Swartz et al. | 607/45 |
| 6,516,227 B1 | 2/2003 | Meadows et al. | |
| 6,845,267 B2 | 1/2005 | Harrison et al. | |
| 6,895,280 B2 | 5/2005 | Meadows et al. | |

(Continued)

OTHER PUBLICATIONS

Annex to Form PCT/ISA/206 Communication Relating to the Results of the Partial International Search for PCT/US2012/037646, Applicant: Boston Scientific Neuromodulation Corporation, Form PCT/ISA/206, dated Jan. 2, 2013 (3pages).

(Continued)

*Primary Examiner* — Edward Moran
*Assistant Examiner* — Michael Carey
(74) *Attorney, Agent, or Firm* — Lowe Graham Jones PLLC; Bruce E. Black

(57) ABSTRACT

A neurostimulation system for management of stimulation safety limits. The system determines a tissue charge injection metric at each electrode, compares the metric to the hard stop charge limit, and prevents the neurostimulator from delivering stimulation energy to the tissue region in accordance based on the comparison. The hard stop limit may be user-programmable or may be automatically modified in response to detection of electrode characteristics. The system may quantitatively notify a user of a value of the injected charge injected into the tissue. The electrodes may be organized into different sets, in which case, the system may directly control tissue charge independently at each of the electrode sets. If current steering is provided, the system may displace the electrical stimulation energy along the tissue region in one direction, while preventing the charge injection value at each of the electrodes from meeting or exceeding the hard stop charge limit.

8 Claims, 13 Drawing Sheets

(56) References Cited

U.S. PATENT DOCUMENTS

| | | |
|---|---|---|
| 6,950,707 B2 | 9/2005 | Whitehurst |
| 6,993,384 B2 | 1/2006 | Bradley et al. |
| 7,539,538 B2 | 5/2009 | Parramon et al. |
| 7,650,184 B2 | 1/2010 | Walter |
| 8,019,439 B2 | 9/2011 | Kuzma et al. |
| 2003/0139781 A1 | 7/2003 | Bradley et al. |
| 2005/0267546 A1 | 12/2005 | Parramon et al. |
| 2006/0025828 A1 | 2/2006 | Armstrong et al. |
| 2007/0038250 A1 | 2/2007 | He et al. |
| 2007/0168004 A1 | 7/2007 | Walter |
| 2007/0168007 A1 | 7/2007 | Kuzma et al. |
| 2007/0255319 A1* | 11/2007 | Greenberg et al. ............... 607/2 |
| 2008/0269839 A1* | 10/2008 | Armstrong ......... A61N 1/37235 607/59 |
| 2009/0198306 A1* | 8/2009 | Goetz et al. ................... 607/59 |
| 2009/0228079 A1* | 9/2009 | Libbus et al. ..... A61N 1/36114 607/63 |
| 2010/0010566 A1* | 1/2010 | Thacker et al. ................ 607/46 |
| 2010/0012140 A1 | 1/2010 | Fitzpatrick |
| 2012/0290038 A1 | 11/2012 | Moffitt et al. |
| 2012/0290039 A1 | 11/2012 | Moffitt et al. |

OTHER PUBLICATIONS

Shannon, R.V. A Model of Safe Levels for Electrical Stimulation, IEEE-TBME, vol. 39, No. 4, pp. 424-426, Apr. 1992.

Office Action dated Mar. 28, 2013 in U.S. Appl. No. 13/470,158, filed May 11, 2012, inventor: Michael A. Moffitt, (6pages).

File History for U.S. Appl. No. 13/470,158, filed May 11, 2012, inventor: Michael A. Moffitt.

File History for U.S. Appl. No. 13/470,326, filed May 13, 2012, inventor: Michael A. Moffitt.

* cited by examiner

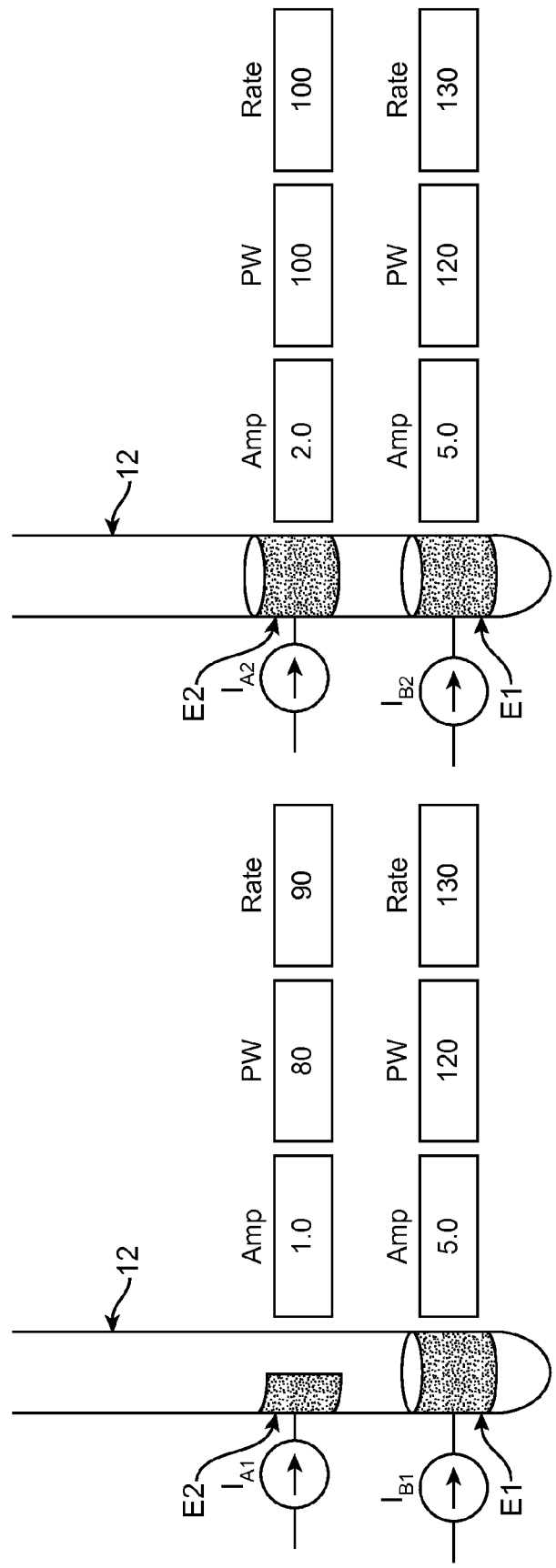

MANAGEMENT OF STIMULATION SAFETY LIMITS IN A NEUROSTIMULATION SYSTEM

RELATED APPLICATION DATA

The present application claims the benefit under 35 U.S.C. §119 to U.S. provisional patent application Ser. No. 61/486,120, filed May 13, 2011. The foregoing application is hereby incorporated by reference into the present application in its entirety.

FIELD OF THE INVENTION

The present invention relates to management of stimulation safety limits, and more particularly, to management of tissue charge safety limits in a neurostimulation system.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. A single stimulation lead may contain electrodes of different sizes. The neurostimulation system may further comprise a handheld external control device to remotely instruct the neurostimulator to generate electrical stimulation pulses in accordance with selected electrical stimulation parameters.

Electrical stimulation energy may be delivered from the neurostimulator to the electrodes in the form of an electrical pulsed waveform. Thus, the stimulation energy may be controllably delivered to the electrodes to stimulate the tissue. The combination of electrodes used to deliver the electrical pulses to the targeted tissue constitutes an electrode combination, with the electrodes capable of being selectively programmed to act as anodes (positive), cathodes (negative), and/or left off (zero). In other words, an electrode combination represents the polarity being positive, negative, or zero. Other parameters that may be controlled or varied include the amplitude, width, and rate of the electrical pulses provided through the electrode array. Each electrode combination, along with its electrical pulse parameters, can be referred to as a "stimulation parameter set."

With some neurostimulation systems, and in particular, those with independently controlled current and/or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e. fractionalized electrode combinations).

As briefly discussed above, an external control device can be used to instruct the neurostimulator to generate electrical stimulation pulses in accordance with selected stimulation parameters. Typically, the stimulation parameters programmed into the neurostimulator can be adjusted by the user by manipulating controls on the external user control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with the set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the amount of non-target tissue that is stimulated. A typical stimulation parameter set may include the electrodes that acting as anodes or cathodes, as well as the amplitude, duration, and rate of the stimulation pulses.

To facilitate the selection of the stimulation parameters, the clinician generally programs the external control device, and if applicable the neurostimulator, through a computerized programming system. This programming system can be a self-contained hardware/software system, or can be defined predominately by software that is run on a standard personal computer (PC). The PC or custom hardware may actively control the characteristics of the electrical stimulation generated by the neurostimulator to allow the optimum stimulation parameters to be determined based on patient feedback, or other means, and to subsequently program the external control device with the optimum electrical stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the disorder or painful site.

Significantly, there are limits to how much charge (both in terms of total charge per pulse (or phase) and charge density per pulse) can be injected into tissue without causing cell trauma and/or electrochemical damage (i.e., corrosion) to the electrodes. Each electrode, depending upon its physical properties (which include, but are not limited to, its size, shape, and material), has a charge threshold level that should not be exceeded to ensure that the amount of charge applied to the electrode will not cause irreparable electrochemical harm to the electrode. Smaller sized electrodes generally have lower charge threshold levels than larger sized electrodes that are manufactured of the same material because the smaller sized electrodes have higher charge densities.

With regard to tissue safety, both total charge and charge density should be taken into account to avoid cell trauma. As such, the Shannon Model was created in 1992 for evaluating tissue safety limits using k-values (k=log(Total Charge)+log (Charge Density)). (See Shannon, R. V., *Model of Safe Levels for Electrical Stimulation*, IEEE-TBME, Vol. 39, No. 4, pp. 424-426, April 1992). The Shannon model indicates that a tissue safety limit of k equal to 1.5 or lower should be maintained to ensure tissue safety.

Previously, a patient undergoing neurostimulation therapy would exhibit side effects well before cell trauma would occur. The onset of side-effects is primarily caused by the total charge per pulse (as well as the charge density per pulse), thereby naturally limiting the total charge per pulse that can be applied to the patient. However, due to the relatively large area, and resulting low charge density, of prior art electrodes, the charge density per pulse was also naturally limited by the side-effects experienced by the patient. However, as the size of electrodes becomes smaller (e.g., the use of segmented electrodes is becoming prevalent in the context of DBS), thereby effectively increasing the charge density per pulse, it is possible to cause cell trauma before the onset of side-effects. It is known to incorporate hard stop limits into neurostimulation systems to ensure that the total charge per pulse injected into the tissue region is within a tissue safety limit. However, these hard stop limits do not take into account charge density per pulse.

Some conventional neurostimulation systems also have warning thresholds that are configured to notify the user that the charge injected into the tissue is at or above a warning threshold by displaying a simple textual notification message. Unlike hard stop limits, these warning thresholds do not necessarily prevent the user from meeting or exceeding the defined safety limit value for tissue charge injection. While, in many cases, the use of warning safety limits for tissue charge injection may warn the user in enough time before tissue damage (and/or electrode damage) occurs, in other cases, the user may desire to have knowledge of the amount of tissue charge injection well before the safety warning threshold is reached.

In addition, most current conventional implantable neurostimulation systems only globally monitor and control the amount of charge that is injected into the tissue. That is, only one electrode (e.g., the worst-case electrode) is monitored, and based on this, the tissue charged injected by all of the electrodes is globally controlled. However, in most cases, the tissue charge injection associated with each active electrode may substantially differ. This is especially the case if different sized electrodes are being used. This is because smaller sized electrodes inherently have a higher charge density than larger sized electrodes, thereby increasing the possibility of tissue damage occurring at these smaller electrodes. Since these conventional neurostimulation systems can only globally monitor and control the tissue charge injection associated with the electrodes, there is a danger that the smaller electrodes may produce stimulation with a charge density high enough to cause damage to the tissue if the tissue charge injection if the warning threshold is set based on a larger electrode, or there is the possibility that the user will be alerted with a notification message too soon if the warning threshold is set based on a smaller electrode.

Additionally, some conventional neurostimulation systems are designed to "steer" electrical current between electrodes in order to move the resultant stimulation region in a defined direction. Typically, these systems proportion the current across the electrodes at various predefined different percentages over time (i.e. steer the current across the electrodes). For example, a system may displace the electrical stimulation energy along the tissue region by incrementally shifting the electrical current from a first group of electrodes to a second group of electrodes, and then from the second group of electrodes to a third group of electrodes, and so on. These systems steer the current without regard to the amount of charge injected within tissue for each incremental shift in the electrical current, thereby posing an increased risk that the charge injected by any particular electrode will damage the tissue, or if one exists, the user may steer the current into the warning limit, thereby reducing the usability of the system.

SUMMARY OF THE INVENTION

In accordance with a first aspect of the present inventions, a neurostimulation system for use with at least one electrode is provided. The neurostimulation system comprises a neurostimulator configured for delivering electrical stimulation energy to a tissue region in accordance with a stimulation parameter, thereby injecting a charge into the tissue region at the electrode(s). The neurostimulation system further comprises an external control device configured for allowing a user to modify the stimulation parameter, and memory storing a hard stop charge limit, which may be programmable. The neurostimulation system further comprises control circuitry, which may entirely be contained in the neurostimulator or entirely contained in the external control device, or portions thereof may be respectively contained in the neurostimulator and external control device.

The control circuitry is configured for determining a tissue charge density injection metric, which may be, e.g., one of a charge density per phase, a k-value, and a charge density per second, and may be one of a relative value, a normalized value, and an absolute value. In one embodiment, the neurostimulator is configured for monitoring the charge injected into the tissue region, and the control circuitry is configured for determining the tissue charge density injection metric based on the monitored charge. In another embodiment, the control circuitry is configured for estimating the tissue charge injection metric based, at least in part, on a stimulation parameter.

The control circuitry is further configured for comparing the tissue charge density injection metric to the hard stop charge limit, and preventing the neurostimulator from delivering the electrical stimulation energy to the tissue region in accordance with the modified stimulation parameter based on the comparison. In one embodiment, the control circuitry is configured for preventing the neurostimulator from delivering the electrical stimulation energy to the region in accordance with the modified stimulation parameter if the tissue charge density injection metric meets or exceeds the hard stop charge limit.

In an optional embodiment, the memory stores a charge warning threshold, in which case, the control circuitry may be configured for comparing the tissue charge injection metric to the charge warning threshold, and the external control device may be configured for providing a user-discernible notification message to the user based on the comparison between the tissue charge injection metric and the charge warning threshold. The external control device may be configured for allowing the user to modify the charge warning threshold, preferably to a value less than the value less than the hard stop limit.

In accordance with a second aspect of the present inventions, another neurostimulation system for use with at least one electrode is provided. The neurostimulation system comprises a neurostimulator configured for delivering electrical stimulation energy to a tissue region, thereby injecting a charge into the tissue region at the at least one electrode, and an external control device configured for being actuated to actively modify the characteristics of the delivered electrical stimulation energy, and for, in response to the modification of the delivered electrical stimulation energy characteristics, quantitatively notifying a user of a value of the charge injected into the tissue.

The charge value may be, e.g., one of a charge per phase, a charge density per phase, a k-value, a charge per second, and a charge density per second, and may be one of a relative value, a normalized value, and an absolute value. In one embodiment, the external control device is configured for quantitatively notifying the user by textually conveying the value of the charge to the user. In another embodiment, the external control device is configured for quantitatively notifying the user by graphically conveying the value of the charge to the user, which may be relative to a charge warning threshold, a hard stop charge limit, and/or a tissue damage threshold.

In accordance with a third aspect of the present inventions, still another neurostimulation system for use with different sets of electrodes is provided. The each of the different sets of electrodes may comprise only a single electrode or can comprise multiple electrodes. The different sets of electrode can be on the same neurostimulation lead or different neurostimulation leads.

The neurostimulation system comprises a neurostimulator configured for delivering electrical stimulation energy to a tissue region in accordance with a stimulation parameter, thereby injecting a charge into the tissue region at the electrodes. The neurostimulation system further comprises an external control device configured for being actuated to actively modify the characteristics of the delivered electrical stimulation energy, and control circuitry configured for directly controlling a value of the tissue charge injection independently at each of the electrode sets. The neurostimulator may be configured for independently conveying electrical current to or from the different sets of electrodes to allow the control circuitry to respectively control the tissue charge injection at the different sets of electrodes. The charge value may be, e.g., one of a charge per phase, a charge density per phase, a k-value, a charge per second, and a charge density per second, and may be one of a relative value, a normalized value, and an absolute value. The control circuitry may, e.g., be contained within the neurostimulator or the external control device.

In one embodiment, the neurostimulator is configured for directly monitoring the value of the tissue charge injection at each of the different sets of electrodes. In another embodiment, the control circuitry configured for estimating a value of the tissue charge injection at each of the different sets of electrodes based, at least in part, on the stimulation parameter. At least two of the electrodes in the respective different sets of electrodes may have different physical properties (e.g., different sizes, different shapes, and/or different materials). In one embodiment, the memory stores different hard stop charge limits for the different sets of electrodes, which the external control device may allow the user to modify. In another embodiment, the memory stores different charge warning thresholds for the different sets of electrodes, which the external control device may allow the user to modify.

In accordance with a fourth aspect of the present inventions, yet another neurostimulation system for use with a plurality of electrodes is provided. The neurostimulation system comprises a neurostimulator configured for delivering electrical stimulation energy to a tissue region, thereby injecting a charge into the tissue region at each of the electrodes, memory storing a hard stop charge limit, and an external control device configured for displacing the electrical stimulation energy along the tissue region in one direction, while preventing a value of the charge injection at each of the electrodes from meeting or exceeding the hard stop charge limit. The charge value may be, e.g., one of a charge per phase, a charge density per phase, a k-value, a charge per second, and a charge density per second, and may be one of a relative value, a normalized value, and an absolute value.

In one embodiment, the external control device is configured for allowing the user to modify the hard stop charge limit. In another embodiment, the external control device is configured for displacing the electrical stimulation energy along the tissue region by incrementally shifting electrical current from a first one of the electrodes to a second one of the electrodes, and when the value of the charge injection at the second electrode reaches the hard stop limit, incrementally shifting the electrical current from the first electrode to a third one of the electrodes to continue to displace the electrical stimulation energy along the tissue region in the one direction.

In accordance with a fifth aspect of the present inventions, still yet another neurostimulation system for use with at least one electrode is provided. The neurostimulation system comprises a neurostimulator configured for delivering electrical stimulation energy to a tissue region in accordance with a stimulation parameter, thereby injecting a charge into the tissue region at the electrode(s). The neurostimulation system further comprises an external control device configured for allowing a user to modify the stimulation parameter, and memory storing a hard stop charge limit, which may be programmable. The neurostimulation system further comprises control circuitry, which may entirely be contained in the neurostimulator or entirely contained in the external control device, or portions thereof may be respectively contained in the neurostimulator and external control device.

The control circuitry is configured for modifying the hard stop charge limit based on a characteristic of the at least one electrode. In one embodiment, the characteristic of the electrode(s) comprises one of a size, shape, and a material. In another embodiment, the electrode(s) is carried by a neurostimulation lead, in which case, the neurostimulation system further comprises monitoring circuitry configured for detecting the type of the neurostimulation lead, and the control circuitry is configured for determining the characteristic of the at least one electrode based on the detected neurostimulation lead type.

The control circuitry is further configured for determining a tissue charge injection metric, which may be, e.g., one of a charge per phase, a charge density per phase, a k-value, a charge per second, and a charge density per second, and may be one of a relative value, a normalized value, and an absolute value. In one embodiment, the neurostimulator is configured for monitoring the charge injected into the tissue region, and the control circuitry is configured for determining the tissue charge injection metric based on the monitored charge. In another embodiment, the control circuitry is configured for estimating the tissue charge injection metric based, at least in part, on a stimulation parameter.

The control circuitry is further configured for comparing the tissue charge injection metric to the hard stop charge limit, and preventing the neurostimulator from delivering the electrical stimulation energy to the tissue region in accordance with the modified stimulation parameter based on the comparison. In one embodiment, the control circuitry is configured for preventing the neurostimulator from delivering the electrical stimulation energy to the region in accordance with the modified stimulation parameter if the tissue charge density injection metric meets or exceeds the hard stop charge limit.

In an optional embodiment, the memory stores a charge warning threshold, in which case, the control circuitry may be configured for modifying the charge warning threshold based on a characteristic of the at least one electrode, and comparing the tissue charge injection metric to the charge warning threshold, and the external control device may be configured for providing a user-discernible notification message to the user based on the comparison between the tissue charge injection metric and the charge warning threshold. The external control device may be configured for allowing the user to modify the charge warning threshold, preferably to a value less than the value less than the hard stop limit.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 13A and 13B are each side views of a neurostimulation lead with electrodes having different stimulation parameters.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
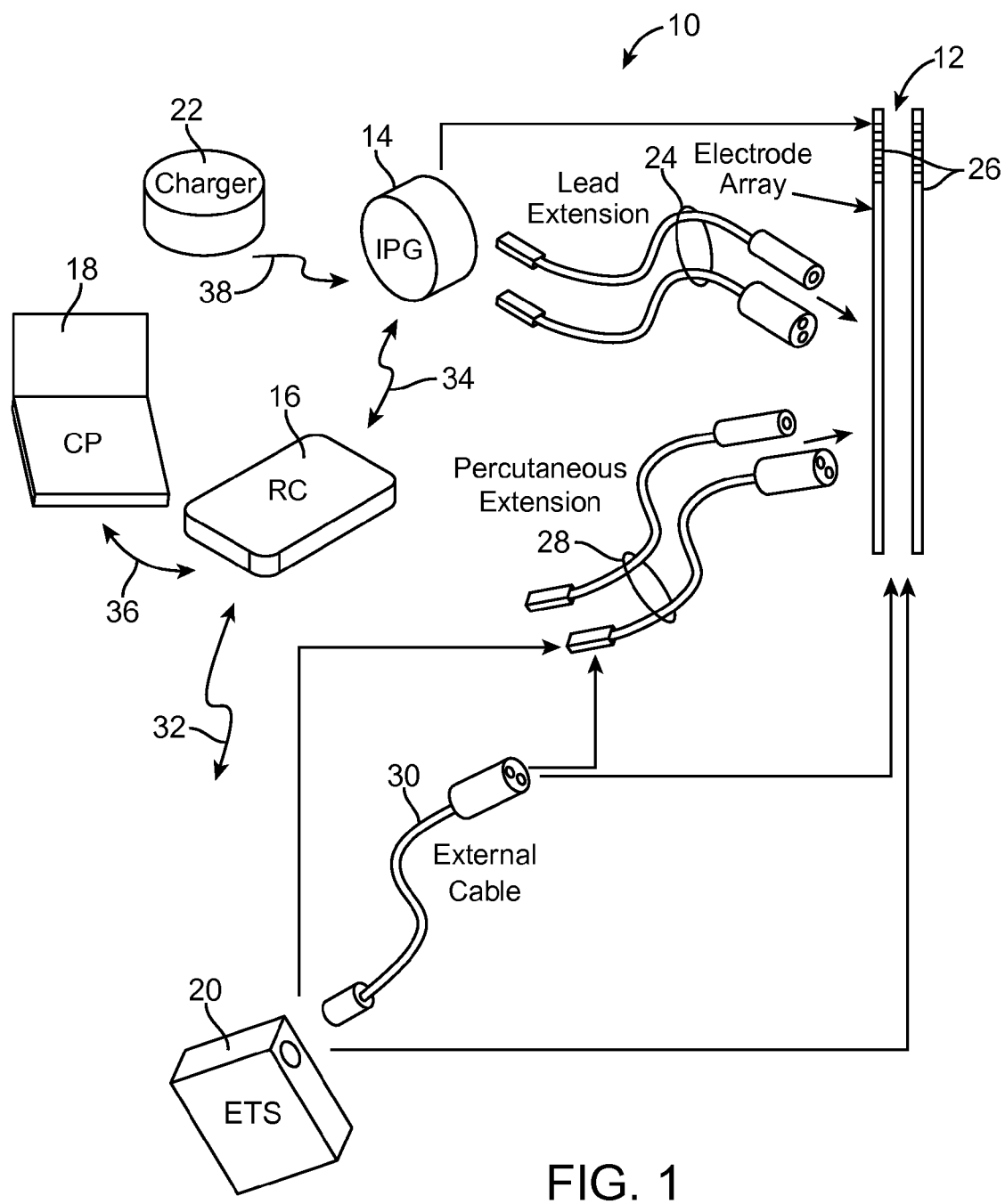
FIG. 1 is block diagram of a deep brain stimulation (DBS) system arranged in accordance with the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (electrodes ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if cortical brain stimulation is desired. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
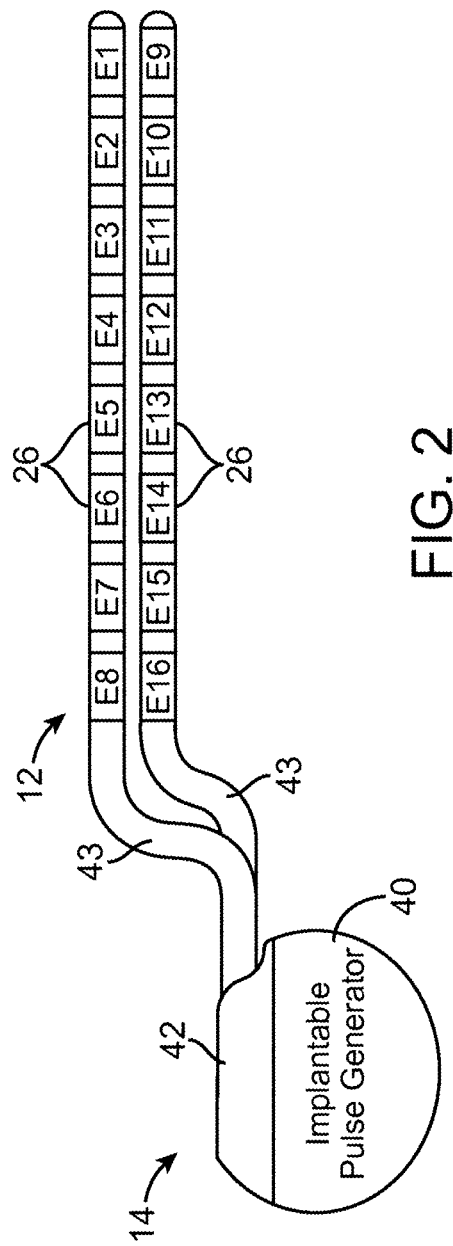
FIG. 2 is a plan view of an implantable pulse generator (IPG) and two percutaneous neurostimulation leads used in the DBS system of FIG. 1.

Referring to FIG. 2, the IPG 14 comprises an outer case 40 for housing the electronic and other components (described in further detail below), and a connector 42 to which the proximal end of the stimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the stimulation leads 12 comprises an elongated cylindrical lead body 43, and the electrodes 26 take the form of ring electrodes mounted around the lead body 43. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the array 22 over multiple channels or over only a single channel.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

Further details discussing the detailed structure and function of IPGs are described more fully in U.S. Pat. Nos. 6,516,227 and 6,993,384, which are expressly incorporated herein by reference.

Figure 3:
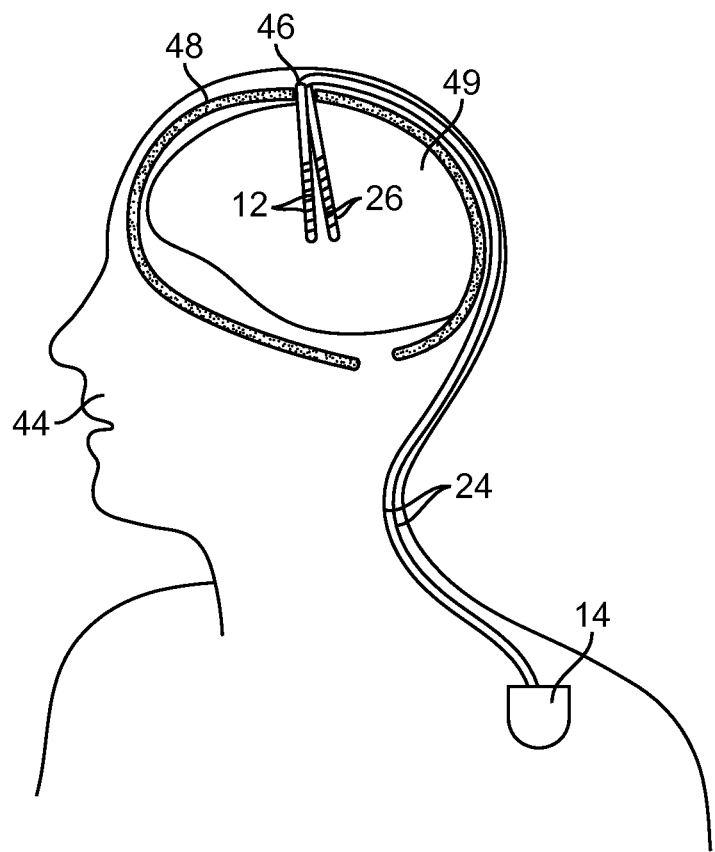
FIG. 3 is a plan view of the DBS system of FIG. 1 in use with a patient.

As shown in FIG. 3, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 4:
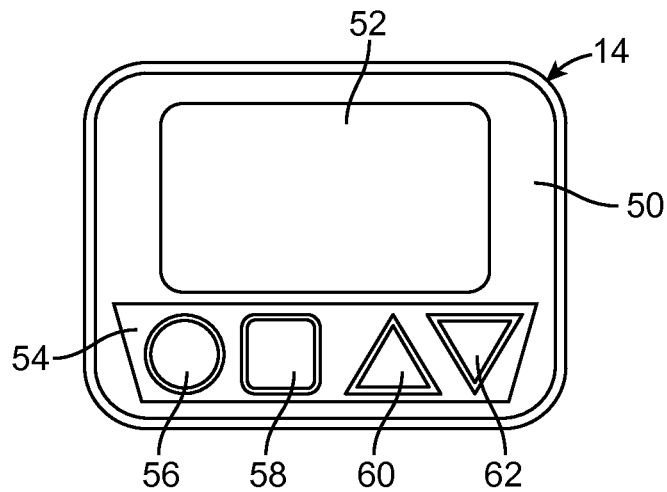
FIG. 4 is front view of a remote control (RC) used in the DBS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
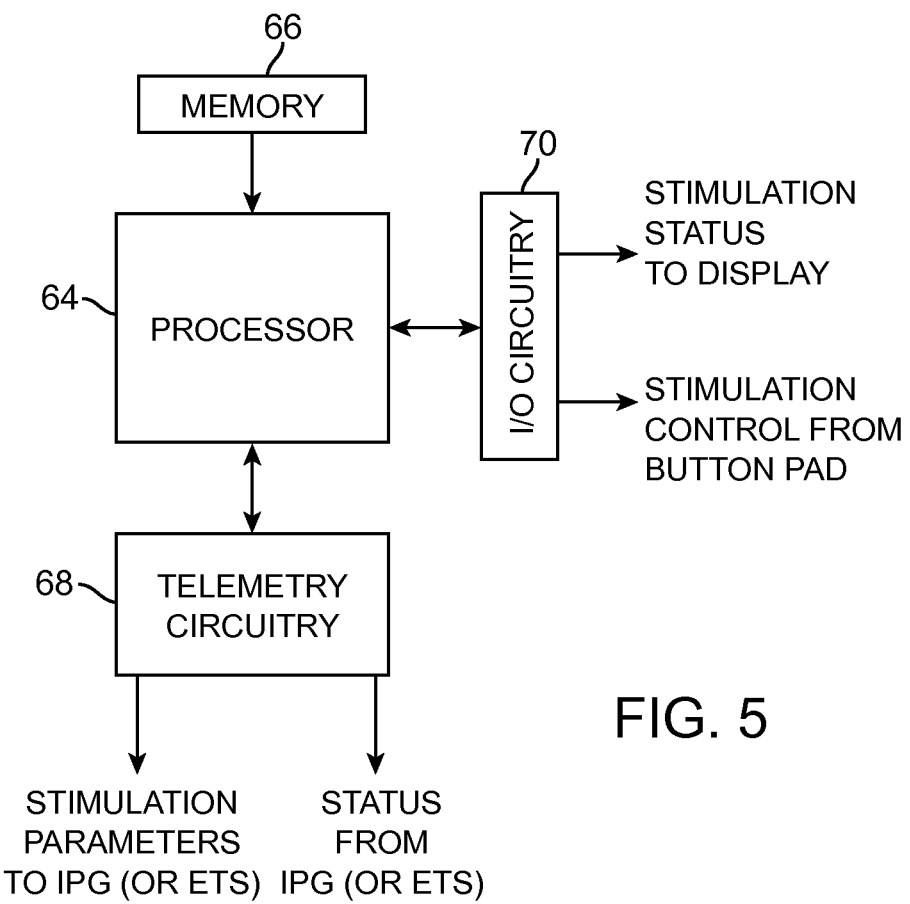
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

Figure 6:
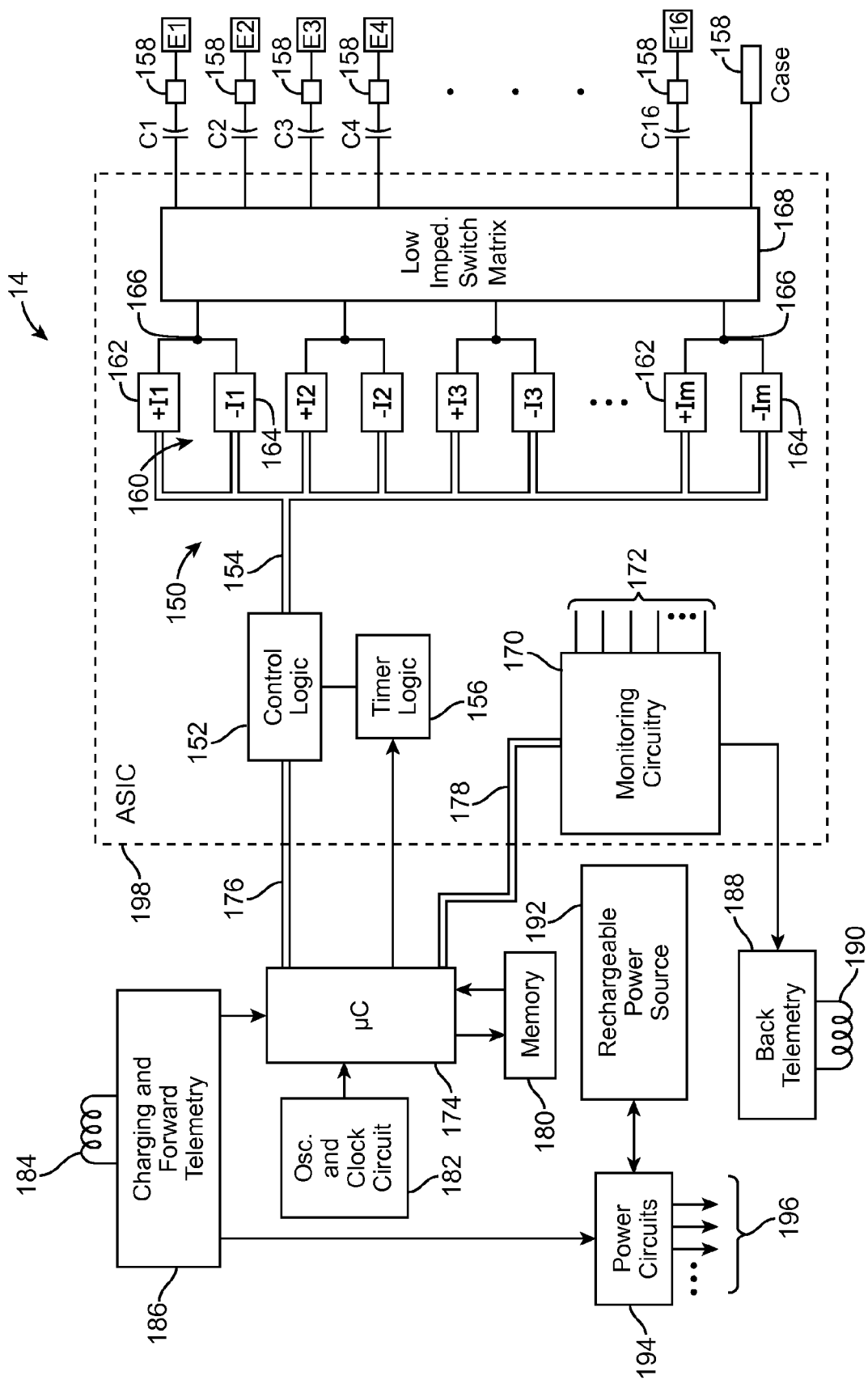
FIG. 6 is a block diagram of the internal components of the IPG of FIG. 2.

Turning next to FIG. 6, one exemplary embodiment of the IPG 14 will now be described. The IPG 14 includes stimulation output circuitry 150 configured for generating electrical stimulation energy in accordance with a defined pulsed waveform having a specified pulse amplitude, pulse rate, and pulse duration under control of control logic 152 over data bus 154. Control of the pulse rate and pulse duration of the electrical waveform is facilitated by timer logic circuitry 156, which may have a suitable resolution, e.g., 10 µs. The stimulation energy generated by the stimulation output circuitry 150 is output via capacitors C1-C16 to electrical terminals 158 corresponding to electrodes E1-E16.

In the illustrated embodiment, the stimulation output circuitry 150 comprises a plurality m independent current source pairs 160 capable of supplying stimulation energy to the electrical terminals 158 at a specified and known amperage. One current source 162 of each pair 160 functions as a positive (+) or anodic current source, while the other current source 164 of each pair 160 functions as a negative (−) or cathodic current source. The outputs of the anodic current source 162 and the cathodic current source 164 of each pair 160 are connected to a common node 166. The stimulation output circuitry 150 further comprises a low impedance switching matrix 168 through which the common node 166 of each current source pair 160 is connected to any of the electrical terminals 158 via the capacitors C1-C16.

Thus, for example, it is possible to program the first anodic current source 162 (+I1) to produce a pulse having a peak amplitude of +4 mA (at a specified rate and for a specified duration), and to synchronously program the second cathodic current source 164 (−I2) to similarly produce a pulse having a peak amplitude of −4 mA (at the same rate and pulse duration), and then connect the node 166 of the anodic current source 162 (−I1) to the electrical terminal 158 corresponding to electrode E3, and connect the node 166 of the cathodic current source 164 (−I2) to the electrical terminal 158 corresponding to electrode E1.

Hence, it is seen that each of the programmable electrical terminals 158 can be programmed to have a positive (sourcing current), a negative (sinking current), or off (no current) polarity. Further, the amplitude of the current pulse being sourced or sunk from a given electrical terminal 158 may be programmed to one of several discrete levels. In one embodiment, the current through each electrical terminal 158 can be individually set from 0 to ±10 mA in steps of 50 µA, within the output voltage/current requirements of the IPG 14. Additionally, in one embodiment, the total current output by a group of electrical terminals 158 can be up to ±20 mA (distributed among the electrodes included in the group). Moreover, it is seen that each of the electrical terminals 158 can operate in a multipolar mode, e.g., where two or more electrical terminals are grouped to source/sink current at the same time. Alternatively, each of the electrical terminals 158 can operate in a monopolar mode where, e.g., the electrical terminals 158 are configured as cathodes (negative), and case of the IPG 14 is configured as an anode (positive).

It can be appreciated that an electrical terminal 158 may be assigned an amplitude and included with any of up to k possible groups, where k is an integer corresponding to the number of timing channels, and in one embodiment, is equal to 4, and with each timing channel k having a defined pulse amplitude, pulse duration, and pulse rate. Other timing channels may be realized in a similar manner. Thus, each channel identifies which electrical terminals 158 (and thus electrodes) are selected to synchronously source or sink current, the pulse amplitude at each of these electrical terminals, and the pulse duration, and pulse rate.

In an alternative embodiment, rather than using independent controlled current sources, independently controlled voltage sources for providing stimulation pulses of a specified and known voltage at the electrical terminals 158 can be provided. The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 170 for monitoring the status of various nodes or other points 172 throughout the IPG 14, e.g., power supply voltages, temperature, battery voltage, and the like. The monitoring circuitry 170 is also configured for measuring electrical data at the electrode array 26 (e.g., electrode impedance, electrode field potential, and/or tissue charge) necessary to determine whether each of the electrodes 26 is functioning properly and is properly coupled to the IPG 14. The monitoring circuitry 170 includes a Coulomb counter that measures the delivery of charge to the tissue region by the electrodes 26 in Coulombs. The Coulomb counter is used to measure or calculate the quantity of charge flowing into the tissue region to thereby provide rates of the charging of the tissue. In particular, the Coulomb counter determines the amount of tissue charge at the electrodes 26 by measuring a voltage drop across a low impedance series resistance on the neurostimulation lead(s) 12.

In cases where the electrode array 26 is used to sense physiological information, the monitoring circuitry 170 may also have the appropriate circuitry (e.g., an analog/digital converter) for converting the physiological information sensed by the electrodes 26 into a form that can be subsequently analyzed. The physiological information at the electrodes 26 may be measured using any one of a variety means, but preferably is made independent of the electrical stimulation pulses, as described in U.S. Pat. Nos. 6,516,227 and 6,993,384, which are expressly incorporated herein by reference.

The IPG 14 further comprises processing circuitry in the form of a microcontroller (μC) 174 that controls the control logic 152 over data bus 176, and obtains status data, and optionally physiological information, from the monitoring circuitry 170 via data bus 178. The IPG 14 also controls the timer logic 156. Alternatively, rather than monitoring the amount of tissue charge, the microcontroller 174 is able to generate an estimate of an amount of tissue charge at each of the electrodes 26 based on the stimulation parameters that are programmed for the electrodes 26. It should be noted that, in addition or alternatively, the processor 80 of CP 18 (refer to FIG. 7) is able to estimate the tissue charge at each of the electrodes 26 based on the programmed electrode stimulation parameters.

In particular, the amount of charge actually delivered in a stimulation pulse is related to the characteristics of the stimulation pulse. When the pulse amplitude characterizes the current amplitude of the stimulation pulses in the stimulus waveform, the amount of charge actually delivered (Q) can be estimated by using Equation 1.

$$Q \approx \text{(pulse amplitude)(pulse duration)} \qquad \text{Equation 1}$$

Equation 1 can be adjusted to accommodate various forms of pulse amplitude. For example, when the pulse amplitude changes over time, Equation 1 can be changed to a time integral that includes the changing pulse amplitude.

Conversely, when the pulse amplitude characterizes the voltage amplitude of the stimulation pulses in the stimulus waveform, the amount of charge actually delivered (Q) can be estimated by using Equation 2.

$$Q \approx \text{(pulse amplitude)(pulse duration)}/(Z) \qquad \text{Equation 2}$$

The impedance Z refers to the electrical impedance of current flow from one electrode 26 through the tissue to another electrode 26. Electrical impedance can vary over time with changes in the electrodes 26 and/or surrounding tissue. For example, the location of an electrode 26 within a moving body can vary over time, the electrical characteristics of tissue at the site of stimulation can vary over time, the electrode 26 itself can become contaminated (e.g., biofouling) or otherwise change over time, or the electrode-electrolyte interface can vary over time.

The impedance Z can be determined repeatedly during the operation of the neurostimulation system 10. Alternatively, the impedance Z can be estimated and programmed into the system 10. Equation 2 can be adjusted to accommodate various forms of pulse amplitude and impedance Z. For example, when the pulse amplitude and/or impedance Z changes over time, Equation 2 can be changed to a time integral that includes the changing pulse amplitude and/or impedance Z. Further details discussing the estimating of the tissue charge at each of the electrodes 26 are disclosed in U.S. Pat. No. 7,801,600, which is expressly incorporated herein by reference.

The IPG 14 further comprises memory 180 and an oscillator and clock circuit 182 coupled to the microcontroller 174. Thus, the microcontroller 174, in combination with the memory 180 and oscillator and clock circuit 182, comprise a microprocessor system that carries out functions in accordance with a suitable program stored in the memory 780. Alternatively, for some applications, the functions provided by the microprocessor system may be carried out by a suitable state machine.

The microcontroller 174 generates the necessary control and status signals, which allow the microcontroller 174 to control the operation of the IPG 14 in accordance with the operating program and stimulation parameters stored in the memory 180. In controlling the operation of the IPG 14, the microcontroller 174 is able to individually generate stimulus pulses at the electrodes 26 using the stimulation output circuitry 150, in combination with the control logic 152 and timer logic 156, thereby allowing each electrode 26 to be paired or grouped with other electrodes 26, including the monopolar case electrode, and to control and modify the polarity, pulse amplitude, pulse rate, pulse duration, and channel through which the current stimulus pulses are provided.

The IPG 14 further comprises an alternating current (AC) receiving coil 184 for receiving programming data (e.g., the operating program and/or stimulation parameters) from the RC 16 in an appropriate modulated carrier signal, and charging and forward telemetry circuitry 186 for demodulating the carrier signal it receives through the AC receiving coil 184 to recover the programming data, which programming data is then stored within the memory 180, or within other memory elements (not shown) distributed throughout the IPG 14.

The IPG 14 further comprises back telemetry circuitry 188 and an alternating current (AC) transmission coil 190 for sending informational data sensed through the monitoring circuitry 170 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 192 and power circuits 194 for providing the operating power to the IPG 14. The rechargeable power source 192 may, e.g., comprise a lithium-ion or lithium-ion polymer battery. The rechargeable battery 192 provides an unregulated voltage to the power circuits 194. The power circuits 194, in turn, generate the various voltages 196, some of which are regulated and some of which are not, as needed by the various circuits located within the IPG 14. The rechargeable power source 192 is recharged using rectified AC power (or DC power converted from AC power through other means, e.g., efficient AC-to-DC converter circuits, also known as "inverter circuits") received by the AC receiving coil 184. To recharge the power source 192, an external charger (not shown), which generates the AC magnetic field, is placed against, or otherwise adjacent, to the patient's skin over the implanted IPG 14. The AC magnetic field emitted by the external charger induces AC currents in the AC receiving coil 184. The charging and forward telemetry circuitry 186 rectifies the AC current to produce DC current, which is used to charge the power source 192. While the AC receiving coil 184 is described as being used for both wirelessly receiving communications (e.g., programming and control data) and charging energy from the external device, it should be appreciated that the AC receiving coil 184 can be arranged as a dedicated charging coil, while another coil, such as coil 190, can be used for bi-directional telemetry.

As shown in FIG. 6, much of the circuitry included within the IPG 14 may be realized on a single application specific integrated circuit (ASIC) 198. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (Dig IC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 6 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 7:
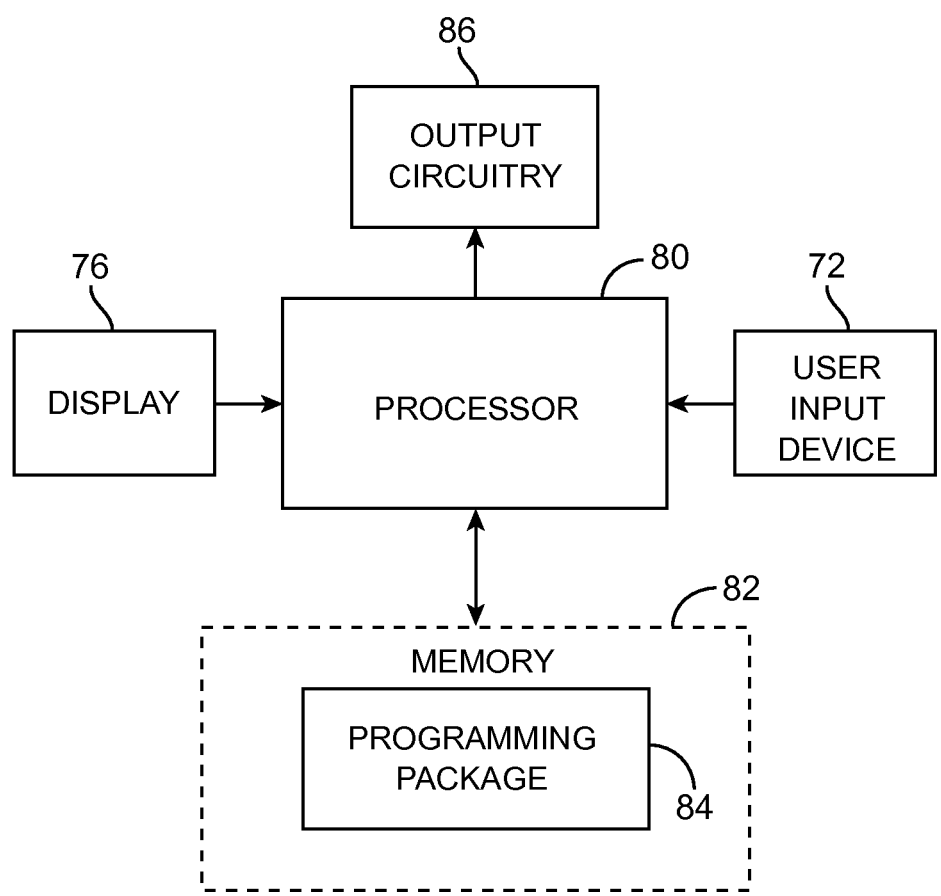
FIG. 7 is a block diagram of the internal components of a clinician's programmer (CP) used in the DBS system of FIG. 1.

Referring to FIG. 7, to allow the user to perform these functions, the CP 18 includes a standard user input device 72 (e.g., a keyboard, mouse, joystick, etc.) to allow a clinician to input information and control the process and a display monitor 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 generally includes a processor 80 (e.g., a central processor unit (CPU)) and memory 82 that stores a stimulation programming package 84, which can be executed by the processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

As discussed in the background, there are limits as to how much charge (both in terms of total charge per pulse (or phase) and charge density per pulse) can be injected into tissue without causing any tissue damage or can be applied to the electrodes without causing any electrochemical damage (i.e. corrosion) to the electrodes. To prevent any possible tissue damage or electrode damage from occurring, the system 10 employs a hard stop limit for preventing the charge injected into the tissue region from meeting or exceeding a charge value defined by the hard stop limit. In particular, the system 10 is configured for comparing a tissue charge injection metric to the charge value defined by the hard stop limit, and preventing the charge injected into the tissue region from meeting or exceeding the charge value based on the comparison. Advantageously, the system 10 does not allow the user to increase the intensity of the electrical stimulation energy if the tissue charge injection metric meets or exceeds the charge value defined by the hard stop limit. In addition, if the tissue charge injection metric meets or exceeds the charge value defined by the hard stop limit, the CP 18 may provide a notification message to the user.

In the illustrated embodiment, the tissue charge injection metric is obtained by monitoring the injection charge of the currently delivered electrical energy, and preventing the further delivery of any electrical energy when the tissue charge injection metric meets the hard stop charge limit. However, in certain embodiments, the tissue charge injection metric can be estimated from a stimulation parameter or parameters selected by the user, so that the electrical energy need not be monitored. In this case, if the tissue charge injection metric meets or even exceeds the hard stop charge limit, the electrical energy in accordance with the stimulator parameter(s) may be prevented from being delivered.

Figure 8:
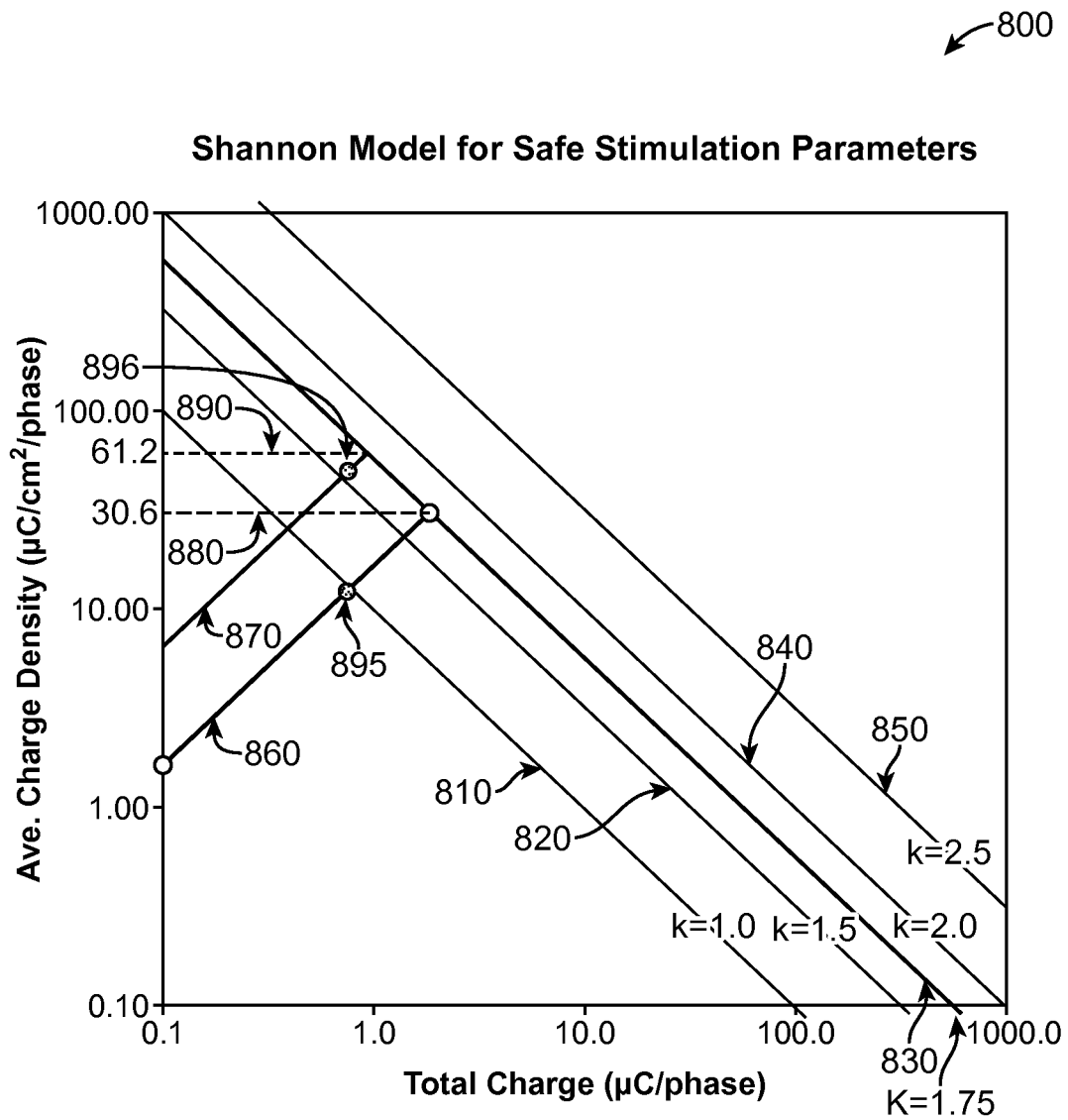
FIG. 8 is a graphical representation of the Shannon model of tissue safety.

The charge value defined by the hard stop limit may be given in terms of a relative value, a normalized value, and/or an absolute value. In addition, the hard stop charge limit can be defined, e.g., by a charge per phase, a charge density per phase, a charge per second, and/or a charge density per second. Preferably, the hard stop charge limit is a function of a charge density (and in the preferred embodiment, the average charge density over the surface of the respective electrode), so that the tissue damage that may otherwise be caused by smaller electrodes can be prevented. The charge value may also be defined by a k-value, which takes into account both total charge and charge density. For example, the Shannon Model is used for evaluating tissue safety limits using k-values. (See Shannon, R. V., *A Model of Safe Levels for Electrical Stimulation*, IEEE-TBME, Vol. 39, No. 4, pp. 424-426, April 1992). FIG. 8 shows the Shannon model 800 for safe tissue charge, which consists of evaluating k=log (Total Charge)+log(Charge Density). The model 800 proposes that for k less than an appropriate safety limit value, the applied electrical stimulation energy is safe for the tissue. In particular, the Shannon model proposes a stimulation safety limit of k equal to 1.5.

The diagonal lines 810, 820, 830, 840, and 850 in FIG. 8 show charge data for several different k-values. The k-value equal to 1.75 (i.e. diagonal 830) corresponds to the widely accepted 30 $\mu C/cm^2$ limit employed by most contemporary DBS devices. Diagonal lines 860 and 870 show the pertinent charge data for two specific electrode sizes, 6 $mm^2$ and 1.5 $mm^2$, respectively. Dashed horizontal lines 880 and 890 each illustrate a corresponding candidate charge density limit for k=1.75 for the given electrode size. Symbols 895 and 896 denote the charge data that corresponds to electrical stimulation of 5 mA and 150 µs for each electrode. When an electrical stimulation of 5 mA and 150 µs was applied to each of these two electrodes, the 6 $mm^2$ electrode yielded an average charge density of 12.5 $\mu C/cm^2$, and the 1.5 $mm^2$ electrode yielded an average charge density of 50 $\mu C/cm^2$. Since the yielded charge density of 12.5 $\mu C/cm^2$ for the 6 $mm^2$ electrode (i.e. the larger electrode) is only ~41% of the theoretical limit of 30.6 $\mu C/cm^2$ for k=1.75, and since the yielded charge density of 50 $\mu C/cm^2$ for the 1.5 $mm^2$ electrode (i.e. the smaller electrode) is ~82% of the theoretical limit of 61.2 $\mu C/cm^2$ for k=1.75, the measured clinical values are expected to be closer to the theoretical safety limits for smaller-sized electrodes than for larger-sized electrodes.

In addition to the hard stop limit, the system 10 also has a warning threshold. In particular, the system 10 is configured to convey a user-discernable warning signal to the user if the charge injected into the tissue region meets or exceeds a charge value defined by the warning threshold. Additionally, it should be noted that the system 10 will not allow the user to program the warning threshold with a charge value that is greater than the charge value defined by the hard stop limit. In addition, the system 10 gives a quantitative notification to the user of the value of the charge that is being injected into the tissue.

In the illustrated embodiment, the hard stop limits and/or warning thresholds are user-programmable to allow the user the flexibility of modifying them from the manufacturer set hard stop limits, which are typically selected to be at the upper threshold of the tissue safety limit and, as such, can sometimes be dangerously close for a physician's comfort level. In alternative embodiments, the IPG 14 may automatically detect the type of neurostimulation leads coupled to it (and thus, the characteristics (e.g., size, shape, material, etc.) of the electrodes carried by the leads), which information could be used by either the IPG 14 or the CP 18 to automatically modify the hard stop limits and/or warning thresholds. In this manner, the user will not have to guess or otherwise take the time to determine what the values of the hard stop limits and/or warning thresholds should be.

The hard stop limits and/or warning thresholds for the electrodes may be programmable by the user into the system 10 through means of a numerical textual entry, up/down arrow push buttons, a touch screen interface, and/or a user audio interface located on the CP 18. In particular, the CP 18 includes a programming screen that enables the user to program their desired stimulation hard stop limit values and/or warning threshold values into the neurostimulation system. This feature is useful if the user would like to be warned of the occurrence of a specific stimulation level when it is reached, or if the user would like to program the electrode(s) to not meeting or exceed a specific stimulation level.

Figure 9:
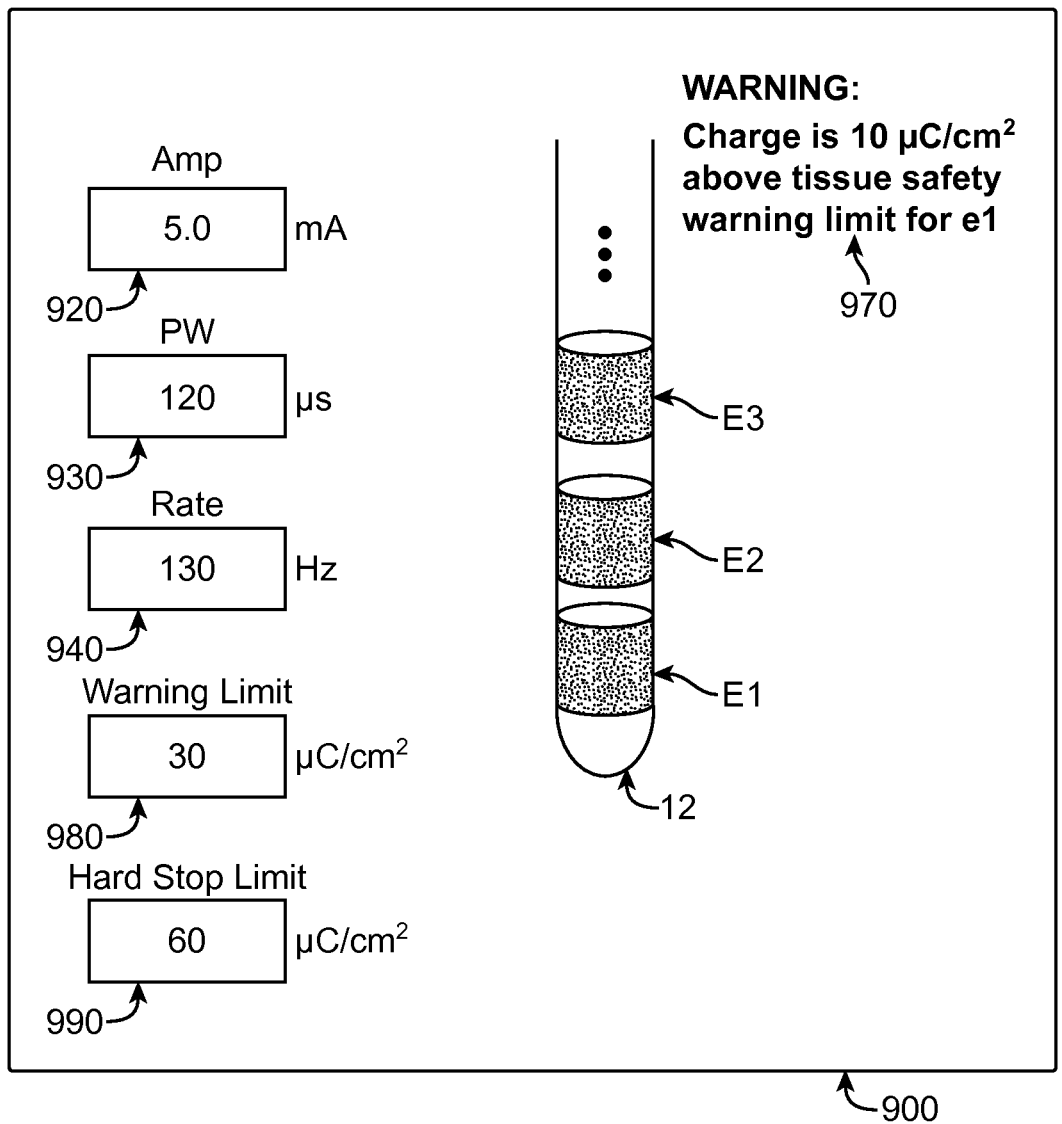
FIG. 9 is a plan view of a programming screen generated by the CP of FIG. 6 showing the textual input programming of a stimulation warning threshold value and a hard stop limit value.

For example, referring to FIG. 9, the programming screen 900 of the CP 18 is shown to have a textual entry user-programmable warning threshold 980 and a textual entry user-programmable hard stop limit 990 as well as a textual entry amplitude 920, pulse width (PW) 930, and rate 940 of the electrical pulses for the electrodes (E1, E2, and E3) 26 on a neurostimulation lead 12. As such, the user is able to program the tissue charge warning threshold value 980, hard stop limit value 990, amplitude 920, PW 930, and rate 940 into the CP 18 by means of numerical textual entries. In addition, the programming screen 900 includes a persistent on-screen indicator 970 (i.e. not a pop-up indicator) with information about the current tissue charge, the current stimulation settings, previous stimulation settings (e.g., settings in a lab reports page), proposed stimulation settings, and/or stimulation settings available to the patient using current patient controller settings. For example, the textual on-screen indicator 970 in FIG. 9 is shown to be indicating that the current tissue charge of 10 μC/cm² is above some warning threshold related to tissue safety for a particular electrode, and in this case, electrode E1.

Indicators may be used to indicate that the settings are at a boundary (i.e. not breaching a limit, but within a step of breaching a limit). In addition, indicators may be used to show a warning threshold, a hard stop limit, a value corresponding to stimulation settings, and/or a relative value of the stimulation settings, which is compared to a hard stop limit and/or a warning threshold threshold. The CP 18 may employ visual indicators (e.g., light emitting diodes (LEDs)), audio indicators, and/or other types of indicators. The indicators are programmed and implemented into the CP 18 of the neurostimulation system via software and/or via hardware.

The neurostimulation system 10 employs manufacturer hard stop limits in addition to the user hard stop limits and user warning thresholds. Generally, the user hard stop limits must be less than or equal to the manufacturer hard stop limits. The neurostimulation system is able to store the hard stop limits and warning thresholds, preferably in the IPG 14 in the memory 780 (refer to FIG. 6). Additionally, the hard stop limits and warning thresholds may be stored in the CP 18 in the memory 82 (refer to FIG. 7). It should be noted that any of the functions of the CP 18 may also be performed by the RC 16.

Figure 10:
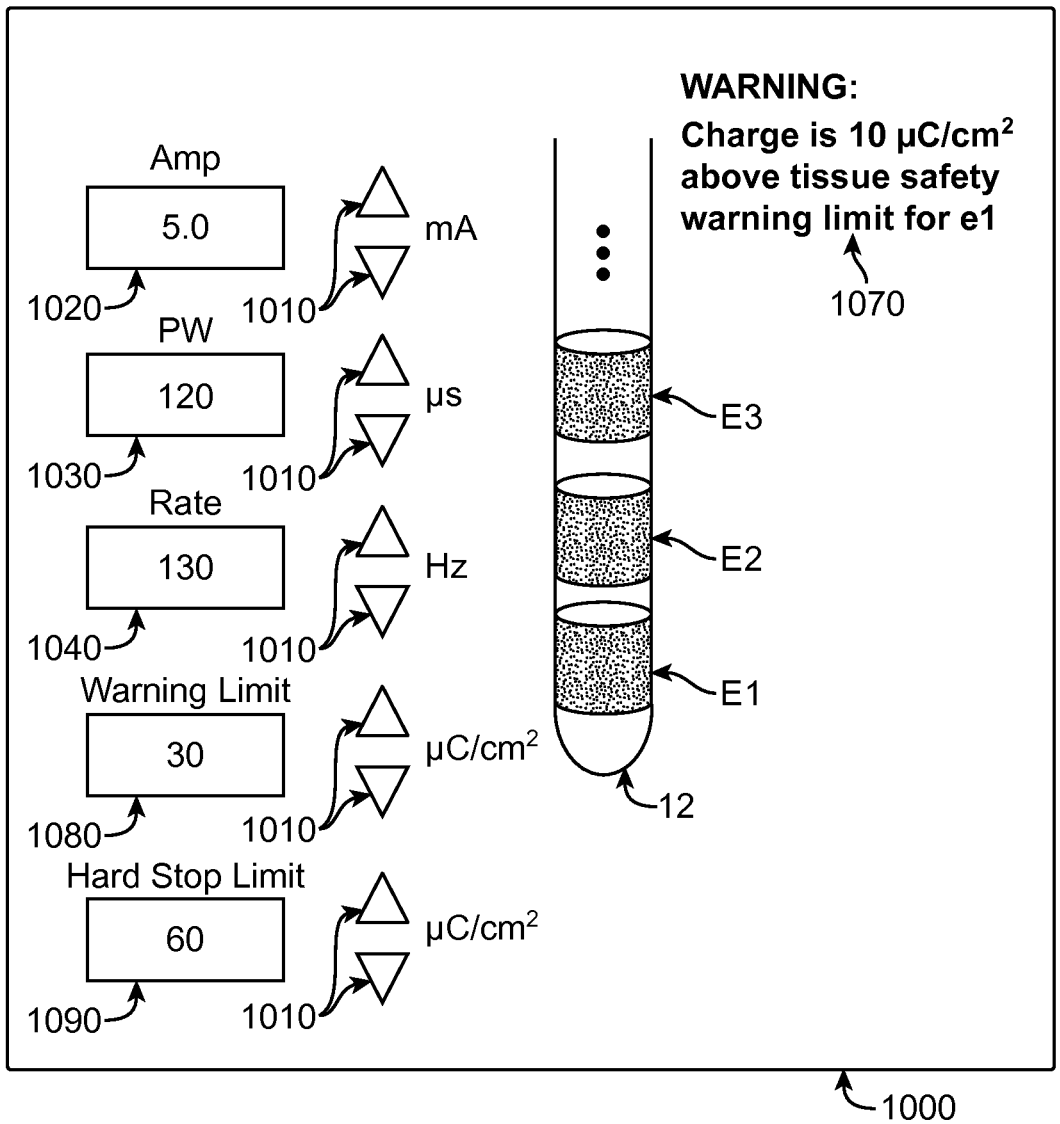
FIG. 10 is a plan view of a programming screen generated by the CP of FIG. 6 showing the programming of a stimulation warning threshold value and a hard stop limit value using up/down arrow buttons.

In another example, referring to FIG. 10, up/down arrow push buttons 1010 are shown on the CP 18 programming screen 1000 to allow a user to program a hard stop limit 1090 and a warning threshold 1080 as well as an amplitude 1020, a PW 1030, and a rate 1040 of the electrical pulses for the electrodes (E1, E2, and E3) 26 on a neurostimulation lead 12. Thus, the user is able to program the tissue charge warning threshold value 1080, hard stop limit value 1090, amplitude 1020, PW 1030, and rate 1040 into the CP 18 by means of depressing the up/down arrow push buttons 1010. Similar to the programming screen 900 of FIG. 9, the programming screen 1000 of FIG. 10 (or alternatively another information screen) is shown to include an on-screen textual indicator 1070 indicating that the current tissue charge density of 10 μC/cm² is above some warning threshold related to tissue safety for a particular electrode, and in this case, electrode E1.

It should be noted that the persistent on-screen indicator 970, 1070 may show the tissue charge status for the "worst-case" electrode (i.e. the electrode experiencing the most significant amount of charge according to the safety limit rule being applied to the system), or conversely may show the tissue charge status for multiple electrodes. In addition, multiple indicators 970, 1070 may be employed by the CP 18 programming screen 900, 1000 to show the status of multiple electrodes, different leads, timing channels, and/or programs. Also, textual visual indicators may be employed by the persistent on-screen indicator 970, 1070 of the disclosed neurostimulation system to show a quantitative comparison of the charge applied to an electrode(s) to a warning threshold and/or a hard stop limit.

Figure 11A:
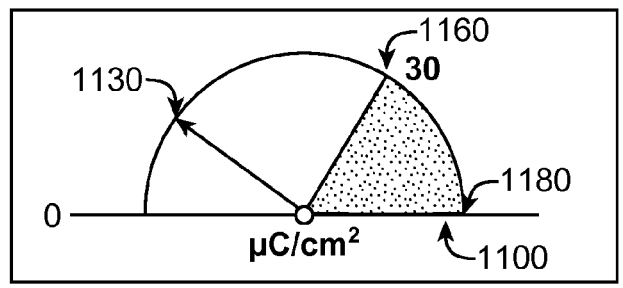
FIGS. 11A-11D are various graphical indicators each showing a stimulation setting compared to a warning threshold and/or hard stop limit.
Figure 11B:
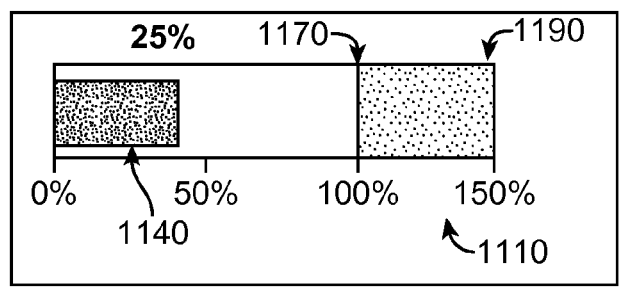
Figure 11C:
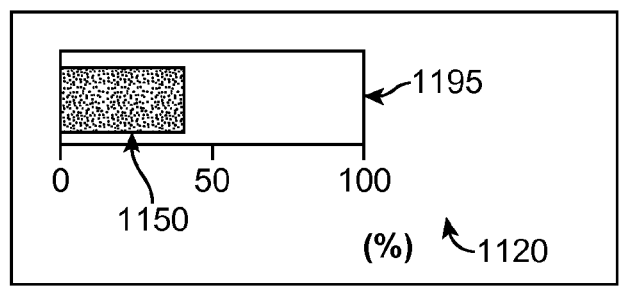
Figure 11D:
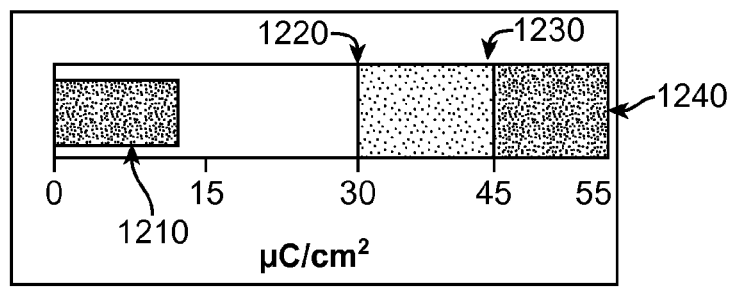

In addition, various types of graphical visual indicators may be employed for the persistent on-screen indicator 970, 1070 of the CP 18 programming screen 900, 1000 (or alternatively, another information screen). For example, referring to FIGS. 11A-11O, different types of graphical indicators are illustrated that show the tissue charge on either an absolute or relative scale, being compared to a warning threshold and/or a hard stop limit. Specifically, graphical indicator 1100 illustrated in FIG. 11A shows a tissue charge 1130 being compared to both a warning threshold 1160 and a hard stop limit 1180. In particular, graphical indicator 1100 is a meter indicator that shows an absolute comparison of the tissue charge density 1130 to the warning threshold 1160 and to the hard stop limit 1180. The graphical indicator 1110 illustrated in FIG. 11B is a bar graph indicator showing a relative percentage comparison of the tissue charge 1140 to a warning threshold 1170 and to a hard stop limit 1190. FIG. 11C illustrates a graphical indicator 1120 that is a bar graph indicator showing a relative percentage comparison of the tissue charge 1150 to only a warning threshold, programmable hard stop limit, or manufacturing hard limit 1195. The graphical indicator 1110 illustrated in FIG. 11D is a bar graph indicator showing an absolute comparison of the tissue charge 1210 to a warning threshold 1220, programmable hard stop limit 1230, and manufacturer-defined hard stop limit 1240. As such, the graphical indicator employed by the persistent on-screen indicator may be used to compare the tissue charge to a warning threshold and/or a hard stop limit (either programmable or manufacturer defined).

Additionally, the neurostimulation system 10 is configured to directly monitor and control a value of the tissue charge injection independently at each of different sets of electrodes 26 on one or more neurostimulation lead 12. In one embodiment, the different sets of electrodes 26 are carried by different neurostimulation leads 12. Each set of electrodes may have only a single electrode or multiple electrodes. In the illustrated embodiment described below, each electrode set has a single electrode.

Figures 12A, 12B:
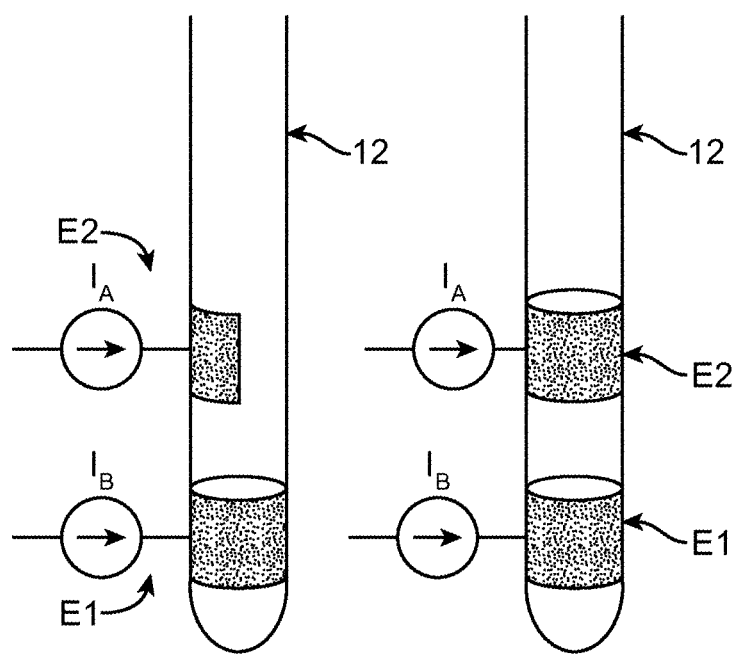
FIGS. 12A and 12B are each side views of a neurostimulation lead having independent and direct control of charge injection through each electrode.

FIGS. 12A and 12B each show independent and direct control of tissue charge injection through a given electrode 26 (E1 and E2) on a neurostimulation lead 12 using independent current sources 162 ($I_A$ and $I_B$) for each electrode 26. Specifically, as shown in these figures, current source $I_A$ supplies current for electrode E2 and current source $I_B$ supplies current for electrode E1. The IPG 14 is configured for independently sourcing electrical current to or from the electrodes 26 to respectively control the tissue charge injection at the electrodes 26. It should be noted that the charge injected in a stimulation phase is the integration of the current for that phase, which for square phases corresponds to a multiplication of the amplitude and the pulse width. Alternatively, in order to control the tissue charge injection at each of the electrodes 26, the IPG 14 may be configured to independently source voltage, instead of current, to the electrodes 26.

It can be appreciated that the manner in which the neurostimulation system 10 controls the tissue charge injection based on the hard stop limit and/or the warning threshold will depend on where the tissue charge injection is monitored or estimated and where the monitored or estimated tissue charge injection is compared to the hard stop limit and/or the warning threshold. For example, in a first embodiment, the IPG 14 both monitors and controls the tissue charge injection at each of the electrodes 26 (refer to FIGS. 6, 12A, and 12B). In particular, the monitoring circuitry 170 of the IPG 14 obtains the tissue charge injection data from the electrodes 26, and sends the tissue charge injection data to the microcontroller 174 via the data bus 178. The microcontroller 174 uses the tissue charge injection data it receives to determine whether the tissue charge injection at each of the electrodes 26 (or the array of electrodes 26) meets or exceeds the hard stop limit and/or the warning threshold previously stored in the memory. It should be noted that the microcontroller 174 receives the hard stop limit and/or warning threshold for the electrodes 26 from the CP 18 via the alternating current (AC) receiving coil 184 and the charging and forward telemetry circuit 186 of the IPG 14. If the microcontroller 174 determines that the amount of tissue charge injection at an electrode(s) 26 has met or exceeded the hard stop limit for that electrode(s) 26, the microcontroller 174 will direct the stimulation output circuitry 150 via the control logic 152 to independently stop or decrease the stimulation at that respective electrode(s) 26. In addition, the microcontroller 174 sends the tissue charge injection data that it has received to the CP 18 via the AC transmission coil 190 and the back telemetry circuit 188 of the IPG 14, which can be displayed to the user, as discussed above.

In a second embodiment, the IPG 14 monitors the tissue charge injection at each of the electrodes 26, while the CP 18 controls the tissue charge injection at each of the electrodes 26. In particular, the monitoring circuitry 170 of the IPG 14 obtains the tissue charge injection data from the electrodes 26, and sends the tissue charge injection data to the CP 18 via the AC transmission coil 190 and the back telemetry circuit 188 of the IPG 14. The output circuitry 86 of the CP 18 (refer to FIG. 7) receives the tissue charge injection data from the IPG 14.

After the CP 18 has received the tissue charge injection data, the processor 80 of the CP 18 (refer to FIG. 7) determines whether the amount of tissue charge injection at an electrode(s) 26 has met or exceeded the hard stop limit and/or the warning threshold for the electrode(s) 26. Once the CP 18 has made this determination(s), the CP 18 transmits control messages regarding how to control the stimulation at that electrode(s) 26 to the IPG 14. The microcontroller 174 of the IPG 14 receives the control messages from the CP 18 via the alternating current (AC) receiving coil 184 and the charging and forward telemetry circuit 186 of the IPG 14.

In a third embodiment, the CP 18 both estimates and controls the tissue charge injection at each of the electrodes 26. In particular, the processor 80 of the CP 18 computes an estimate of the tissue charge injection at each of the electrodes 26 based on the programmed stimulation parameters, and the processor 80 of the CP 18 determines whether the amount of tissue charge injection at an electrode(s) 26 has met or exceeded the hard stop limit and/or the warning threshold for the electrode(s) 26. After the CP 18 makes this determination(s), the CP 18 sends control messages to the IPG 14 to independently control the stimulation at the electrode(s) 26.

In a fourth embodiment, the CP 18 estimates the tissue charge injection at each of the electrodes 26 and the IPG 14 controls the tissue charge injection at each of the electrodes 26. In particular, the CP 18 computes an estimate of the tissue charge injection at each of the electrodes 26 based on the programmed stimulation parameters, and sends the tissue charge injection data to the IPG 14 via the output circuitry 86 of the CP 18. The microcontroller 174 of the IPG 14 receives the tissue charge injection data from the CP 18 via the alternating current (AC) receiving coil 184 and the charging and forward telemetry circuit 186 of the IPG 14. If the microcontroller 174 determines that the amount of tissue charge injection at an electrode(s) 26 has met or exceeded the hard stop limit for that electrode(s) 26, the microcontroller 174 will direct the stimulation output circuitry 150 via the control logic 152 to independently stop or decrease the stimulation at that respective electrode(s) 26.

It should be noted that the microcontroller 174 of the IPG 14 may regulate the electrodes 26 differently (e.g., uses different hard stop limits and/or warning thresholds for the different electrodes 26) based on the different physical properties of the electrodes 26. The different physical properties of the electrodes 26 taken into consideration include, but are not limited to, electrode surface area, electrode size, electrode shape, and/or electrode material. Regulating the electrodes (E1 and E2) on neurostimulation lead 12 in FIG. 12A differently would be appropriate because electrode E2 is smaller in size than electrode E1. Smaller sized electrodes inherently have less surface area than larger sized electrodes and, therefore, smaller sized electrodes are more likely to provide stimulation with a higher charge density to the tissue than larger sized electrodes, thereby increasing the possibility of tissue damage and electrode damage occurring at these smaller electrodes. As such, smaller-sized electrode E2 should have a lower hard stop limit and/or lower warning threshold than larger-sized electrode E1, as can be appreciated from FIG. 8. The user is able to program the various different hard stop limits and/or warning thresholds for each of the electrodes 26.

For example, referring to FIGS. 13A and 13B, the different electrodes 26 are shown to have different stimulation settings. In particular, each electrode has its own amplitude, PW, and rate limit setting. Specifically, in these figures, electrode E2 in FIG. 13A is shown to have an amplitude limit of 1.0 mA, a PW limit of 80 µs, and a rate limit of 90 Hz; electrode E1 in FIG. 13A is shown to have an amplitude limit of 5.0 mA, a PW limit of 120 µs, and a rate limit of 130 Hz; electrode E2 in FIG. 13B is shown to have an amplitude limit of 2.0 mA, a PW limit of 100 µs, and a rate limit of 100 Hz; and electrode E1 in FIG. 13B is shown to have an amplitude limit of 5.0 mA, a PW limit of 120 µs, and a rate limit of 130 Hz.

Alternatively, the neurostimulation system 10 may regulate all of the electrodes on a lead (e.g., electrodes 26 (E1 and E2) on lead 12 in FIG. 13A or electrodes 26 (E1 and E2) on lead 12 in FIG. 13B) the same. For this type of regulation, conservative hard stop limits and/or warning thresholds that are appropriate for any electrode on the neurostimulation lead are employed.

Additionally, the neurostimulation system 10 may be configured to "steer" electrical current between the electrodes 26 in order to move the resultant stimulation region in a defined direction while preventing a value of the charge injection at each of the electrodes from meeting or exceeding a charge value defined by a hard stop limit. The IPG 14 displaces (i.e. "steers") the electrical stimulation energy along the tissue region by first incrementally shifting electrical current from a first electrode to a second electrode. When the value of the charge injection at the second electrode reaches the charge value defined by the hard stop limit, the IPG 14 incrementally shifts the electrical current from the first electrode to a third electrode. The IPG 14 then continues this process for all of the remaining electrodes 26. In at least one embodiment, the hard stop limit is user programmable.

Figure 14:
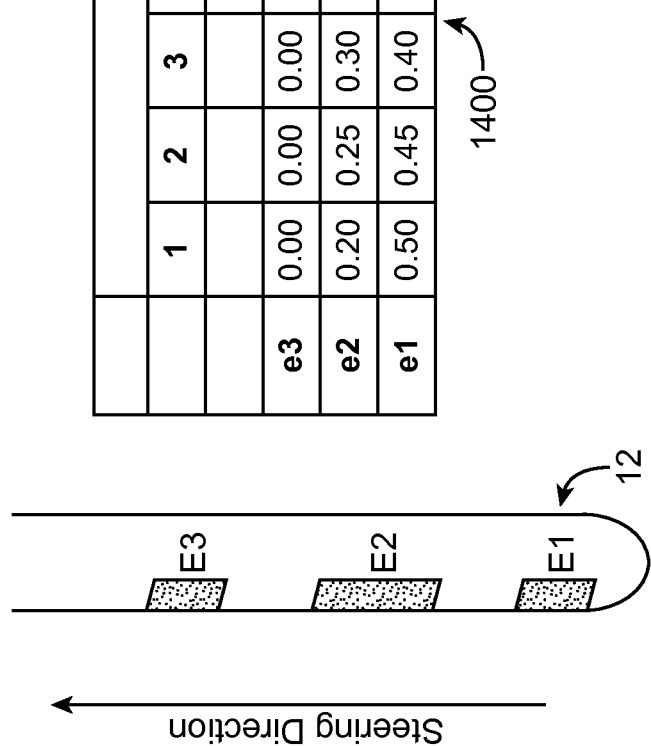
FIG. 14 is table showing the output of a current-steering algorithm for an exemplary lead with three electrodes that manages stimulation safety level.

The neurostimulation system 10 may use a current-steering algorithm to "steer" the electrical stimulation energy between the electrodes 26, which may be similar to the current steering algorithms discussed in U.S. Pat. No. 6,052,624, with the difference being that the charge on each electrode is limited. For example, referring to FIG. 14, the output charges 1400 of three electrodes 26 (E1, E2, and E3) being controlled by a specific current-steering algorithm are shown. The current-steering algorithm automatically prevents the charge injection on a given electrode 26 from meeting or exceeding a warning threshold and/or a hard stop limit, while continuing to steer current in an appropriate direction. As illustrated in FIG. 14, a hard stop limit value of 0.5 µC is chosen for each of the three electrodes 26 on the neurostimulation lead 12. Initially, the steering direction proceeds from electrode E1 to electrode E2. When the charge injection at electrode E2 reaches the charge value of the hard stop limit (i.e. 0.5 µC), the algorithm adjusts and moves current from electrode E1 to electrode E3, thereby leaving the charge level at electrode E2 at the hard stop limit value. On-screen and/or on-device indicators (e.g., 970 and 1070 of FIGS. 9 and 10, respectively) may be used to inform the user of the charge levels at each of the electrodes 26. These indicators would allow for feedback from the user acknowledging that an electrode(s) 26 had reached the charge value of the hard stop limit. The hard stop limit used by the algorithm may be programmed by the manufacturer of the neurostimulation system 10 and/or may be user-programmable, as discussed above.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system for concurrent use with a plurality of electrodes, comprising:
    a neurostimulator configured for delivering electrical stimulation energy to a tissue region, thereby injecting a charge into the tissue region at each of the electrodes;
    memory storing a hard stop charge limit; and
    an external control device configured for displacing the electrical stimulation energy along the tissue region in one direction, while preventing a value of the charge injection at each of the electrodes from meeting or exceeding the hard stop charge limit.

2. The neurostimulation system of claim 1, wherein the value of the charge injection is one of a charge density per phase, a k-value, and a charge density per second.

3. The neurostimulation system of claim 1, wherein the value of the charge injection is in terms of one of a relative value, a normalized value, and an absolute value.

4. The neurostimulation system of claim 1, wherein the external control device is configured for displacing the electrical stimulation energy along the tissue region by incrementally shifting electrical current from a first one of the electrodes to a second one of the electrodes, and when the value of the charge injection at the second electrode reaches the hard stop limit, incrementally shifting the electrical current from the first electrode to a third one of the electrodes to continue to displace the electrical stimulation energy along the tissue region in the one direction.

5. The neurostimulation system of claim 1, wherein the external control device is configured for allowing the user to modify the hard stop charge limit.

6. A neurostimulation system for use with at least one electrode, comprising:
    a neurostimulator configured for delivering electrical stimulation energy to a tissue region in accordance with a stimulation parameter, thereby injecting a charge into the tissue region at the at least one electrode;
    an external control device configured for allowing a user to modify the stimulation parameter;
    memory storing a hard stop charge limit; and
    control circuitry configured for modifying the hard stop charge limit based on a characteristic of the at least one electrode, determining a tissue charge injection metric at the at least one electrode, comparing the tissue charge injection metric to the modified hard stop charge limit, and preventing the neurostimulator from delivering the electrical stimulation energy to the tissue region in accordance with the modified stimulation parameter based on the comparison, wherein the characteristic of the at least one electrode comprises one of a size, shape, and a material.

7. A neurostimulation system for use with at least one electrode, comprising:
    a neurostimulator configured for delivering electrical stimulation energy to a tissue region in accordance with a stimulation parameter, thereby injecting a charge into the tissue region at the at least one electrode;
    an external control device configured for allowing a user to modify the stimulation parameter;
    memory storing a hard stop charge limit; and
    control circuitry configured for modifying the hard stop charge limit based on a characteristic of the at least one electrode, determining a tissue charge injection metric at the at least one electrode, comparing the tissue charge injection metric to the modified hard stop charge limit, and preventing the neurostimulator from delivering the electrical stimulation energy to the tissue region in accordance with the modified stimulation parameter based on the comparison, wherein the at least one electrode is carried by a neurostimulation lead, and the neurostimulation system further comprises monitoring circuitry configured for detecting the type of the neurostimulation lead, and the control circuitry is configured for determining the characteristic of the at least one electrode based on the detected neurostimulation lead type.

8. The neurostimulation system of claim 6, wherein the control circuitry is configured for determining the characteristic of the at least one electrode, and automatically modifying the hard stop charge limit in response to determining the characteristic of the at least one electrode.

\* \* \* \* \*